United States Patent
Li et al.

(10) Patent No.: US 7,781,468 B2
(45) Date of Patent: Aug. 24, 2010

(54) TYROSINE DERIVATIVES SUBSTITUTED BY N-ARYLACRYLOYL AS AGONISTS OF HPPAR ALPHA AND/OR HPPAR GAMMA

(75) Inventors: Song Li, Beijing (CN); Xinbo Zhou, Beijing (CN); Lili Wang, Beijing (CN); Cheng Xu, Beijing (CN); Chengmai Ruan, Beijing (CN); Cuifang Lin, Beijing (CN); Junhai Xiao, Beijing (CN); Zhibing Zhen, Beijing (CN); Hongying Liu, Beijing (CN); Yunde Xie, Beijing (CN); Zhong Wu, Beijing (CN); Hao Cui, Beijing (CN)

(73) Assignee: Beijing Molecule Science Technology Co., Ltd., Beijing (CN)

( * ) Notice: Subject to any disclaimer, the term of this patent is extended or adjusted under 35 U.S.C. 154(b) by 677 days.

(21) Appl. No.: 11/597,656

(22) PCT Filed: Mar. 2, 2005

(86) PCT No.: PCT/CN2005/000256

§ 371 (c)(1),
(2), (4) Date: Aug. 16, 2007

(87) PCT Pub. No.: WO2005/115999

PCT Pub. Date: Dec. 8, 2005

(65) Prior Publication Data

US 2008/0300286 A1    Dec. 4, 2008

(30) Foreign Application Priority Data

May 24, 2004    (CN)    ................ 2004 1 0042574

(51) Int. Cl.
*A61K 31/421*    (2006.01)
*C07D 263/30*    (2006.01)

(52) U.S. Cl. ........................... 514/374; 548/236

(58) Field of Classification Search .............. None
See application file for complete search history.

(56) References Cited

U.S. PATENT DOCUMENTS 5,478,852 A    12/1995    Olefsky et al.

FOREIGN PATENT DOCUMENTS

| WO | WO/00/08002 | 2/2000 |
| WO | 01/16120 | 3/2001 |
| WO | 02/28821 | 4/2002 |
| WO | 02/100403 | 12/2002 |

*Primary Examiner*—Kamal A Saeed
(74) *Attorney, Agent, or Firm*—Ladas and Parry LLP

(57) ABSTRACT

The present invention relates to a compound of formula I, racemates, optically active isomers, or pharmaceutically acceptable salts or solvates thereof, and a pharmaceutical composition comprising the compound, the various radicals in the formula I are the same as defined in the claims. The present invention also relates to a process for preparing the compound of formula I and use of said compound in the preparation of a medicament for the treatment of hyperglycemia, dyslipidemia, type II diabetes mellitus including associated diabetic dyslipidemia

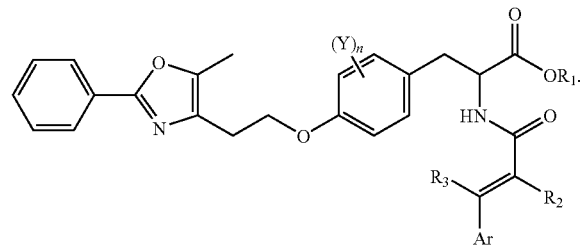

10 Claims, No Drawings

TYROSINE DERIVATIVES SUBSTITUTED BY N-ARYLACRYLOYL AS AGONISTS OF HPPAR ALPHA AND/OR HPPAR GAMMA

FIELD OF THE INVENTION

The present invention relates to substituted tyrosine derivatives substituted by N-arylacryloyl or pharmaceutically acceptable salts or solvates thereof, processes for preparing them, pharmaceutical composition comprising them, and their use, as agonists of peroxisome proliferator-activated receptor (abbreviated as PPAR), in particular as double agonists of PPARγ and PPARα, for the prevention and/or treatment of metabolic diseases such as diabetes and hyperlipidemia.

BACKGROUND OF THE INVENTION

Peroxisome Proliferator Activated Receptors (PPAR's), alike glucocorticoid receptors, tretinoin receptors and thyroid receptors, are ligand-dependent transcription factors pertaining to intranuclear receptor superfamily. PPAR can be subdivided into three subtypes: PPARα, PPARγ and PPARδ (also known as PPARβ and NUC1), which are encoded by different genes. Moreover, PPARγ also have two isoforms, i.e., PPARγ$_1$ and PPARγ$_2$. These two proteins differ in their 30 amino acids at NH$_2$-terminal, which are resulted from the alternative use of promoter and the differential splicing of nRNA (Vidal-Puig, J. Clin. Invest., 97:2553-2561, 1996).

PPARα is mainly expressed in the tissues, such as brown adipose tissue and liver, having high catabolic capacity for lipids, followed by kidney, heart and skeletal muscle (Endocnnology, 1995, 137, 354). It can positively or negatively control the expression of genes related to the metabolism and the intracellular transport of fatty acid (e.g. acyl CoA synthetase, fatty acid-binding protein and lipoprotein lipase) and of apolipoprotein (AI, AII, CIII) genes related to the metabolisms of cholesterol and neutral lipids PPARγ is found at high levels in adipose tissue and at lower levels in skeletal muscle, liver, colon, retina and immune system. Recently, it was found at high levels in macrophages, including atherosclerorotic foam cell. Of which, PPARγ$_2$ was specifically expressed predominantly in adipose tissue. In contrast, PPARγ$_1$ had a broad tissue expression, and was expressed at the highest levels in kidney, intestines and heart. PPARγ serves as a key regulator for adipocyte differentiation and expression of insulin-sensitive genes (J. Lipid Res., 1996, 37, 907).

PPARδ is expressed ubiquitously in the tissues of organisms with nerve cells as the center. At present, the physiological significance of PPARδ is still unclear.

Thiazolidinedione drugs, for example troglitazone and rosiglitazone, were clinically shown to be capable of enhancing insulin-action and reducing serum glucose in patients with Type 2 diabetes. It has been reported that thiazolidinediones are potent and selective activators of PPARγ and bind directly to the PPARγ receptor (J. M. Lehmann, et. al., J. Biol. Chem. 2953-12956, 270 (1995)).

Fibrates were widely used as a class of drugs for treating hyperlipidemia, which might lower serum triglycerides by 20-50%, lower LDLc by 10-15%, and increase HDLc by 10-15%. Experimental evidence indicated that the effects of fibrates on serum lipids were mediated through activation of PPARα. See, for example, B. Staels, et al., Curr. Pharm. Des., 7-14, 3(1), (1997). Activation of PPARα resulted in transcription of enzymes that increased fatty acid catabolism and decreased fatty acid re-synthesis in the liver (leading to decrease of triglyceride synthesis and VLDL production/secretion). In addition, activation of PPARα decreased production of apoC-111. The reduction in production of apoC-111 (an inhibitor of LPL activity) increased clearance of VLDL (J. Auwerx, et al., Atherosclerosis, J59-S37, 124 (Suppl), (1996)).

The results of the existing technology showed that a dual agonist of PPARα and PPARγ had additional advantage for reducing other abnormality, in particular increased triglyceride, concomitant with diabetes. See, for example, U.S. Pat. No. 5,478,852, WO 98/05331.

CONTENTS OF THE INVENTION

The object of the present invention is to search and develop a small molecular compound as agonist of PPARα and PPARγ, which compound is effective for treating PPARα and/or PPARγ mediated diseases, risk factors or disorders. After research, the present inventor discovers that the compound having the following general formula I is an agonist of PPARα and PPARγ, and therefore is effective for preventing and/or treating diseases or symptoms, e.g., diabetes or hyperglycemia, associated with PPARα and PPARγ. The inventor further discovers that the compound of formula I also has an excellent lipid-reducing effect.

Therefore, in one aspect, the present invention relates to compounds of the general formula I, racemates, optically active isomers, or pharmaceutically acceptable salts or solvates thereof,

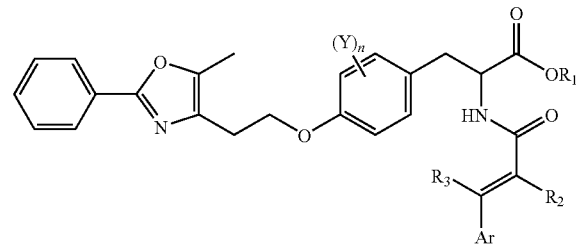

wherein

R$_1$ is selected from hydrogen, C$_1$-C$_4$ straight or branched alkyl;

R$_2$ and R$_3$ are independently selected from hydrogen, halogen, C$_1$-C$_4$ straight or branched alkyl;

Ar is selected from mono-, di-, or tricyclic aromatic carbocyclic ring or heterocyclic ring containing 1 to 4 heteroatoms selected from a group consisting of O, S and N, wherein each single ring is 5- or 6-membered ring, and said ring may be unsubstituted or substituted with 1 to 5 of the following groups: halogen, nitro, hydroxy, hydroxymethyl, trifluoromethyl, trifluoromethoxy, C$_1$-C$_6$ straight or branched alkyl, C$_2$-C$_6$ straight or branched alkenyl, C$_1$-C$_4$ alkoxy, C$_2$-C$_4$ alkenoxy, phenoxy, benzyloxy, carboxyl or amino;

Y is hydrogen or halogen:

n is an integer from 1 to 4.

In another aspect, the present invention relates to a pharmaceutical composition comprising at least one compound of formula I, or racemate, optically active isomer or pharmaceutically acceptable salt or solvate thereof, and one or more pharmaceutically acceptable carriers or excipients.

In another aspect, the present invention provides a process for preparing the compounds of Formula I or pharmaceutically acceptable salts or solvates thereof.

In still another aspect, the present invention relates to use of the compound of formula I in the manufacture of a medicament for the treatment or prevention of PPARα and/or PPARγ mediated diseases, risk factors or conditions.

The hPPARγ and/or hPPARα mediated diseases, risk factors, or conditions include hyperglycemia, dyslipidemia, type II diabetes mellitus including associated diabetic dyslipidemia, type I diabetes, hypertriglyceridemia, syndrome X, insulin resistance, heart failure, hyperlipidemia, hypercholesteremia, hypertension, cardiovascular disease including atherosclerosis, regulation of appetite and food intake in subjects suffering from conditions such as obesity, anorexia, bulimia, and anorexia nervosa.

Specifically, in one embodiment, the present invention relates to compounds of the general formula I, racemates, optically active isomers, or pharmaceutically acceptable salts or solvates thereof,

I

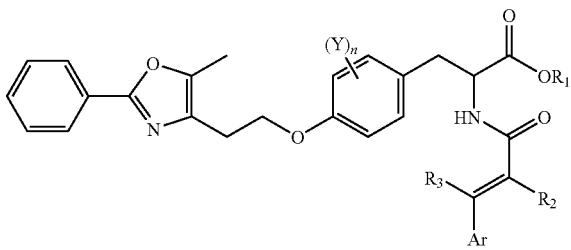

wherein $R_1$ is selected from hydrogen, $C_1$-$C_4$ straight or branched alkyl;

$R_2$ and $R_3$ are independently selected from hydrogen, halogen, $C_1$-$C_4$ straight or branched alkyl;

Ar is selected from mono-, di-, or tricyclic aromatic carbocyclic ring or heterocyclic ring containing 1 to 4 heteroatoms selected from a group consisting of O, S and N, wherein each single ring is 5- or 6-membered ring, and said ring may be unsubstituted or substituted with 1 to 5 of the following groups: halogen, nitro, hydroxy, hydroxymethyl, trifluoromethyl, trifluoromethoxy, $C_1$-$C_6$ straight or branched alkyl, $C_2$-$C_4$ straight or branched alkenyl, $C_1$-$C_4$ alkoxy, $C_2$-$C_4$ alkenoxy, phenoxy, benzyloxy, carboxyl or amino;

Y is hydrogen or halogen;

n is an integer from 1 to 4.

In one preferred embodiment, the compounds of formula I are S-configuration isomers of formula II, or pharmaceutically acceptable salts or solvates thereof,

II

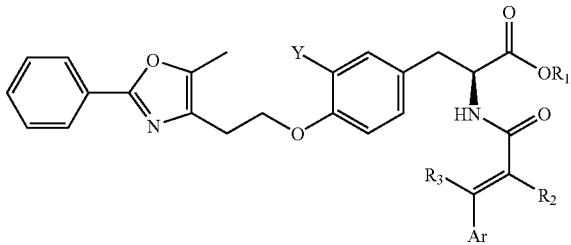

wherein:

carbon atom bonded to $COOR_1$ is in the S configuration;

$R_1$ is selected from hydrogen, $C_1$-$C_4$ straight or branched alkyl;

$R_2$ and $R_3$ are independently selected from hydrogen, halogen, $C_1$-$C_4$ straight or branched alkyl;

Ar is selected from mono-, di-, or tricyclic aromatic carbocyclic ring or heterocyclic ring containing 1 to 4 heteroatoms selected from a group consisting of O, S and N, wherein each single ring is 5- or 6-membered ring, and said ring may be unsubstituted or substituted with 1 to 5 of the following groups: halogen, nitro, hydroxy, hydroxymethyl, trifluoromethyl, trifluoromethoxyl, $C_1$-$C_6$ straight or branched alkyl, $C_2$-$C_6$ straight or branched alkenyl, $C_1$-$C_4$ alkoxy, $C_2$-$C_4$ alkenoxy, phenoxy, benzyloxy, carboxyl or amino;

Y is hydrogen or bromo.

Preferred compounds of the present invention are selected from:

(2S)-3-{4-[2-(5-methyl-2-phenyl-1,3-oxazol-4-yl)-ethoxy]-phenyl}-2-(3-phenyl-acryloylamino)-propionic acid;

(2S)-2-(2-fluoro-3-phenyl-acryloylamino)-3-{4-[2-(5-methyl-2-phenyl-1,3-oxazol-4-yl)-ethoxy]-phenyl}-propionic acid;

(2S)-2-[3-(4-fluorophenyl)acryloylamino]-3-(4-(2-(5-methyl-2-phenyl-1,3-oxazol-4-yl)ethoxy)-phenyl)-propanoic acid;

(2S)-3-{4-[2-(5-methyl-2-phenyl-1,3-oxazol-4-yl)-ethoxy]-phenyl)-2-(3-(2-(trifluoromethyl)phenyl)acryloylamino)-propanoic acid;

(2S)-2-[3-(3-chlorophenyl)acryloylamino]-3-{4-[2-(5-methyl-2-phenyl-1,3-oxazol-4-yl)-ethoxy]-phenyl}-propanoic acid;

(2S)-3-{4-[2-(5-methyl-2-phenyl-1,3-oxazol-4-yl)-ethoxy]-phenyl}-2-[3-(3-(trifluoromethyl)-phenyl)-acryloylamino]-propanoic acid;

(2S)-2-[3-(3,4-difluorophenyl)-acryloylamino]-3-{4-[2-(5-methyl-2-phenyl-1,3-oxazol-4-yl)-ethoxy]-phenyl}-propanoic acid;

(2S)-2-[3-(2,4-difluorophenyl)-acryloylamino]-3-{4-[2-(5-methyl-2-phenyl-1,3-oxazol-4-yl)-ethoxy]-phenyl}-propanoic acid;

(2S)-2-(3-(furan-2-yl)acryloylamino)-3-{4-[2-(5-methyl-2-phenyl-1,3-oxazol-4-yl)-ethoxy]-phenyl}-propanoic acid;

(2S)-3-{3-bromo-4-[2-(5-methyl-2-phenyl-1,3-oxazol-4-yl)-ethoxy]-phenyl}2-(3-p-tolylacryloylamino)-propanoic acid;

(2S)-3-{3-bromo-4-[2-(5-methyl-2-phenyl-1,3-oxazol-4-yl)-ethoxy]-phenyl}-2-(2-fluoro-3-phenyl-acryloylamino)propionic acid;

(2S)-3-{3-bromo-4-[2-(5-methyl-2-phenyl-1,3-oxazol-4-yl)-ethoxy]-phenyl}-2-[3-(2,4-difluorophenyl)acryloylamino]-propanoic acid;

(2S)-3-{3-bromo-4-[2-(5-methyl-2-phenyl-1,3-oxazol-4-yl)-ethoxy]-phenyl}-2-(2-fluoro-3-phenyl-acryloylamino)-propionic acid;

or pharmaceutically acceptable salts and solvates thereof.

The compounds of formula I, or pharmaceutically acceptable salts or solvates thereof, wherein $R_1$, $R_2$, $R_3$, Ar, Y and n are the same as defined above for formula I, may be synthesized by reacting a compound of formula III

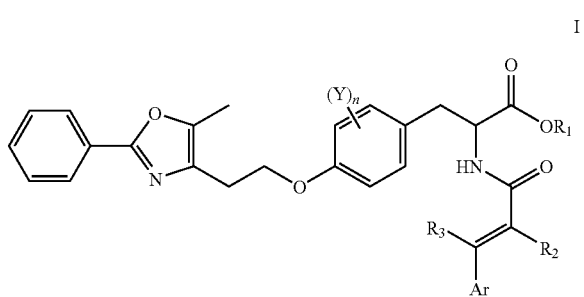

wherein Y, n and $R_1$ are the same as defined above for formula I, and Ph is phenyl;

with a compound of formula X,

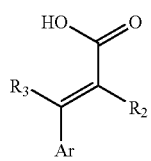

wherein Ar, $R_2$ and $R_3$ are the same as defined above for formula I.

The compound of formula III as one of raw materials may be prepared by the following method:

1) subjecting benzamide, which is commercially available, and a compound of formula IV to a ring closure reaction to thereby obtain a compound of formula V; reducing the compound of formula V with lithium aluminum hydride (LiAlH$_4$) to obtain a compound of formula VI; the compound of formula IV may be prepared by referring to Chem. Pharm. Bull. (1986), 34(7), 2840-51; and J. Med. Chem. (1992), 35(14), 2617-26;

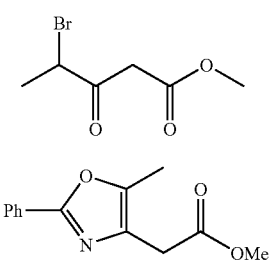

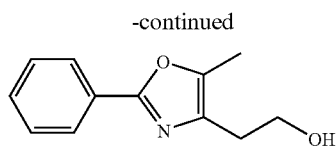

2) reacting a compound of formula VII (wherein Y and n are the same as defined above for formula I, preferably Y is hydrogen or n is 1 and Y is Br in the ortho position of hydroxy group), with $R_1$OH (wherein $R_1$ is the same as defined above for formula I, preferably $R_1$ is methyl) and thionyl chloride (SOCl$_2$), followed by reacting with di-tert-butyl dicarbonate (BOC$_2$O), to give a compound of formula VIII (wherein $R_1$, Y and n are the same as defined above for formula I); the compound of formula VII wherein n is 1 and Y is Br in the ortho position of hydroxy group may be prepared from the reaction of tyrosine with bromine;

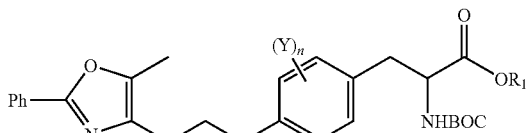

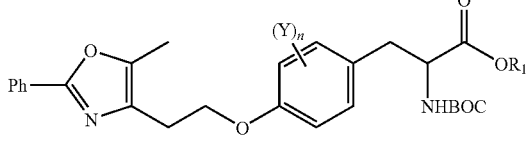

3) reacting the compound of formula VI obtained in the step 1) with the compound of formula VIII obtained in the step 2) to obtain a compound of formula IX,

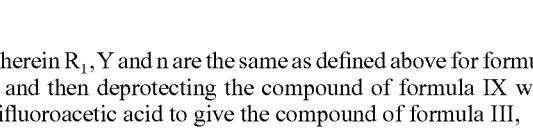

wherein $R_1$, Y and n are the same as defined above for formula I; and then deprotecting the compound of formula IX with trifluoroacetic acid to give the compound of formula III,

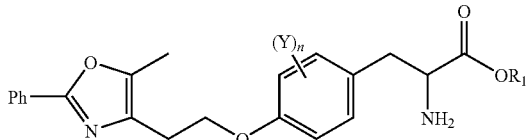

wherein $R_1$, Y and n are the same as defined above for formula I.

Unless indicated, another raw material, the compound of formula X, is purchased from Aldrich company, USA.

If desired, a compound of formula I can be converted to another compound of formula I in a different form. For example, a compound of formula I, wherein $R_1$ represents hydrogen, may be obtained by reacting, a compound of formula I wherein $R_1$ represents $C_1$-$C_4$ straight or branched alkyl, with an alkali metal hydroxide.

More concretely, the compounds of formula I can be synthesized through the following route:

Step 1:

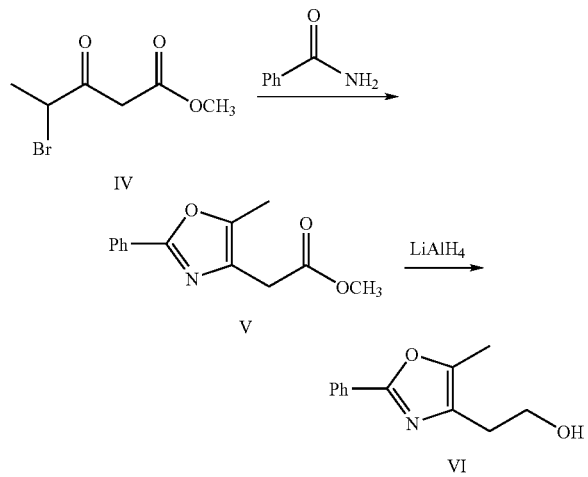

A compound of formula IV reacts with benzamide (purchased from Beijing Chemical Reagent Co.) for 6-30 h under the condition of reflux in toluene, followed by concentration and purification with silica gel column chromatography (using n-hexane/EtOAc as an eluent), to obtain a compound of formula V as brown oil. The compound of formula V reacts with LiAlH$_4$ (purchased from Huanwei Fine Chemicals Co., Tianjin) in Et$_2$O at room temperature for 1-24 h, to which water, NaOH aqueous solution and anhydrous MgSO$_4$ are carefully dropped in turn, followed by stirring for 0.1-1 h. The resulting solution is filtered, and then the filtrate is concentrated and purified by silica gel column chromatography (using n-hexane/EtOAc as an eluent) to obtain a compound of formula VI as a white solid. Silica gel used herein is silica gel used for conventional column chromatography with particle size of 10-40 μm.

Step 2:

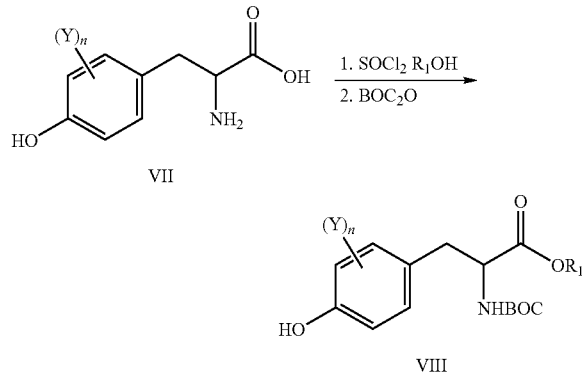

wherein Y, n and $R_1$ are the same as defined above for formula I.

A compound of formula VII (wherein, preferably, Y is hydrogen or n is 1 and Y is Br in the ortho position of hydroxy group) is refluxed for 1 to 10 h with $R_1$OH (wherein, $R_1$ is preferably CH$_3$) and SOCl$_2$, followed by concentration. The obtained residue reacts with BOC$_2$O for 1 to 8 h at room temperature in anhydrous CH$_3$CN under the catalysis of triethylamine, before concentration. The obtained product is dissolved with dichloromethane, washed with NaHSO$_4$ aqueous solution, saturated sodium carbonate aqueous solution and saturated brine in turn, and then dried. After concentration and recrystallization with ethyl ether, a compound of formula VIII is obtained as a white solid. The compound of formula VIII wherein n is 1 and Y is Br in the ortho position of hydroxy group may be prepared from the reaction of tyrosine and bromine in glacial acetic acid at −20-110° C. for 0.5 to 48 h.

Step 3:

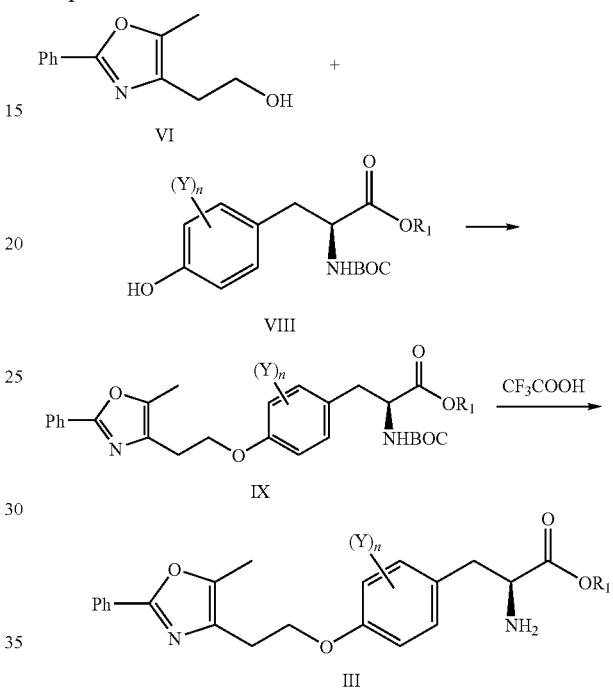

wherein Y, $R_1$ and n are the same as defined above for Formula I.

A compound of formula VI reacts, according to Mitsunobu-type method, with a compound of formula VIII in the presence of triphenylphosphine (PPh$_3$) and azodicarboxylic acid ester such as azodicarboxylic diethyl ether in an organic solvent such as THF at −20-150° C. (e.g., 20° C.) for 1 to 40 h, followed by concentration and purification with silica gel column chromatography (using n-hexane/EtOAc as an eluent), to obtain a compound of formula IX. The compound of formula IX reacts with trifluoroacetic acid in an organic solvent such as CH$_2$Cl$_2$ at −20-40° C. for 1 to 40 h. The reaction mixture is neutralized with NaOH aqueous solution.

The organic layer is dried, concentrated, and then purified with silica gel column chromatography (using CHCl$_3$/MeOH as an eluent) to give the compound of formula III.

Step 4:

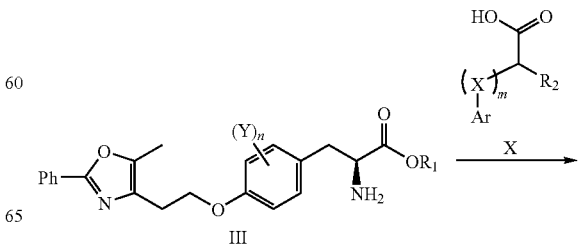

-continued

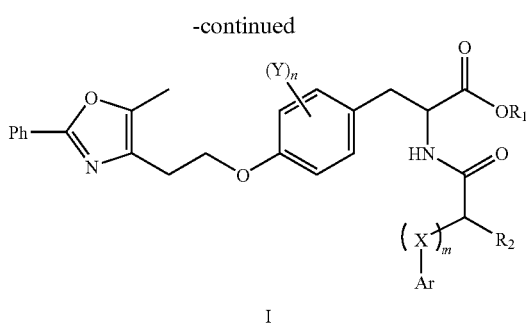

I wherein $R_1$, $R_2$, $R_3$, Ar, Y and n are the same as defined above for formula I.

A compound of formula X reacts with thionyl chloride ($SOCl_2$) at 0-80° C. for 0.5 to 10 h, followed by evaporating thionyl chloride. The resulting residue is dissolved in anhydrous dichloromethane, which is then dropped at −20-40° C. to an anhydrous dichloromethane solution containing a compound of formula III and triethylamine, before stirring at room temperature for 0.1-20 h. The reaction solution is concentrated and purified with silica gel column chromatography (using n-hexane/EtOAc as an eluent) to give the compound of formula I.

If desired, a compound of formula I can be converted to another compound of formula I in a different form. For example, the compound of formula I where $R_1$ represents hydrogen is prepared by reacting the compound of formula I wherein $R_1$ represents $C_1$-$C_4$ straight or branched alkyl in the presence of an alkali metal hydroxide at room temperature or under the condition of reflux for 0.1 to 40 h, before treating.

Those skilled in the art shall recognize that the compound of formula I has a stereocenter. When a compound of formula I is desired as a single enantiomer, it is prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, for resolving the diastereomeric salts formed with chiral acids such as mandelic acid, camphorsulfonic acid, tartaric acid, lactic acid, and the like wherever applicable or with chiral bases such as brucine, cinchona alkaloids and their derivatives and the like. Commonly used methods are listed in "Enantiomers, Racemates and Resolution" (Wiley Interscience, 1981) as compiled by Jaques, et al. More specifically, the compound of formula I may be converted to a 1:1 mixture of diastereomeric amides by treating with chiral amines, amino acids, or amino alcohols derived from amino acids; an acid may be converted into an amide by using conventional reaction conditions; diastereomers may be separated either by fractional crystallization or chromatography, and stereoisomers of the compound of formula I may be prepared by hydrolysing pure diastereomeric amides.

According to the present invention, the compound of formula I can be used for the treatment or prevention of hPPARγ and/or hPPARα mediated diseases, risk factors or conditions. The hPPARγ and/or hPPARα mediated diseases, risk factors, or conditions include hyperglycemia, dyslipidemia, type II diabetes mellitus including associated diabetic dyslipidemia, type I diabetes, hypertriglyceridemia, syndrome X, insulin resistance, heart failure, hyperlipidemia, hypercholesteremia, hypertension, cardiovascular disease including atherosclerosis, regulation of appetite and food intake in subjects suffering from conditions such as obesity, anorexia, bulimia, and anorexia nervosa. In particular, the compound of the present invention is useful in the treatment or prevention of hyperglycaemia, dyslipidemia, and type II diabetes mellitus including associated diabetic dyslipidemia.

The compounds of the present invention may be utilized by themselves, or in the form of pharmaceutically acceptable salts or solvates thereof. The physiologically acceptable salts of the compound of formula I include conventional salts formed from pharmaceutically acceptable inorganic or organic acids or bases as well as quaternary ammonium acid addition salts. The specific examples of suitable acid addition salts include hydrochloric, hydrobromic, sulfuric, phosphoric, nitric, perchloric, fumaric, acetic, propionic, succinic, glycolic, formic, lactic, malefic, tartaric, citric, pamoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be used to prepare salts useful as intermediates for obtaining the compounds of the invention and their pharmaceutically acceptable salts. The specific examples of suitable basic salts include sodium, lithium, potassium, magnesium, aluminum, calcium, zinc, N,N'-dibenzylethylenediamine, chloroprocaine, choline, diethanolamine, ethylenediamine, N-methylglucamine and procaine salts. References to a compound according to the invention include both compounds of formula I and their pharmaceutically acceptable salts or solvates.

The Invention also includes prodrugs of the present compounds, which upon administration undergo chemical conversion by metabolic processes in vivo before becoming active drugs. In general, such prodrugs are functional derivatives of the present compounds, which are readily convertible in vivo into the required compound of formula I. Conventional procedures for the selection and preparation of suitable prodrug derivatives are described, for example, in "Design of Prodrugs", ed. H. Bundgaard, Elsevier, 1985.

The invention also includes active metabolites of the present compounds.

The present compounds can be utilized alone or in the form of pharmaceutical composition. The pharmaceutical composition comprises an effective amount of a compound of formula I, a racemate, an optically active isomer, or a pharmaceutically acceptable salt or solvate thereof, and one or more suitable pharmaceutically acceptable carriers. The pharmaceutically acceptable carrier is selected from, but is not limited to, ion exchanger, aluminum oxide, aluminum stearate, lecithin, serum protein (e.g. human serum protein), buffer substance (e.g. phosphate), glycerol, sorbic acid, potassium sorbate, mixture of partial glycerides of saturated vegetable fatty acids, water, salt or electrolyte (e.g. protamine sulfate, disodium hydrogen phosphate, potassium hydrogen phosphate, sodium chloride, zinc salt), colloidal silicon oxide, magnesium trisilicate, polyvinylpyrrolidone, cellulose, polyethylene glycol, carboxymethycellulose sodium, polyacrylate, beeswax, and lanolin.

The pharmaceutical composition comprising the compound according to the invention may be administered orally, by inhalation spray, rectally, nasally, buccally, topically, parenterally (such as, subcutaneous, intravenous, intramuscular, intraperitoneal, intrachecal, intraventricular, intrasteral, and intracranial injection or infusion), or via an implanted reservoir, preferably orally, intraperitoneally, or intravenously.

When administered orally, the compound of the invention may be produced in any orally acceptable formulation forms comprising, but being not limited to, tablets, capsules, aqueous solutions or aqueous suspensions. Typically, the carriers used for tablets include lactose and corn starch. In addition, lubricating agents such as magnesium stearate may also be added. Usually, diluents used for capsules include lactose and dried corn starch. Aqueous suspension formulations generally include mixture of suitable emulsifying and suspending agents with the active ingredient. If desired, the oral formulation forms may further comprise sweetening agents, flavoring agents or coloring agents.

When administered topically, especially when the conditions addressed for treatment involve areas or organs readily accessible by topical application, including neurological conditions of eye, skin, or lower intestinal tract, the compounds of the invention may be prepared into different topical administration formulations in accordance with the areas or organs.

For topical application to eyes, the compounds of the invention can be formulated as micronized suspensions or solutions in isotonic, pH adjusted sterile saline, either with or without a preservative such as benzylalkonium chloride. Alternatively, for the ophthalmic uses, the compounds may also be formulated in an ointment such as petrolatum.

For topical application to the skin, the compounds can be formulated in a suitable ointment, lotion or cream, wherein the active ingredient suspends or dissolves in one or more carriers. The carriers suitable for ointment include, but are not limited to, mineral oil, liquid petrolatum, white petrolatum, propylene glycol, polyoxyethylene, polyoxypropylene, emulsifying wax and water; and the carriers suitable for lotion or cream include, but are not limited to, mineral oil, sorbitan monostearate, Tween 60, cetyl ester wax, cetearyl alcohol, 2-octyldodecanol, benzyl alcohol and water.

The compounds of the present invention may be administered in the form of sterile injection preparations, for example, as sterile injection aqueous or oleaginous suspensions or sterile injection solutions. The acceptable carriers and solvents include water, Ringer's solution and isotonic sodium chloride solution. In addition, sterile, fixed oils, such as mono- or di-glycerides, can be also employed as solvents or suspending mediums.

In addition, the dosage level and usage method of the present compound depend upon a variety of factors including, the age, body weight, gender, natural health condition, and nutritional status of the subject, the activity of the specific compound employed, the time of administration, the rate of metabolism, the severity of the particular disease being treated, and the subjective judgment of the doctor for diagnosis. The dosage levels on the order of about 0.01 mg to about 100 mg of the active ingredient/kg body weight/day are preferred, while the optimal dosage levels are 5 mg to 10 mg of the active ingredient/kg body weight/day.

MODE OF CARRYING OUR THE INVENTION

The following examples are preferred illustrative examples of the invention, which do not intend to limit the present invention.

Melting points are determined with a RY-1 melting point apparatus and the temperatures are not rectified. $^1$H NMR spectra are recorded on a Bruker ARX 400 NMR spectrometer or on a US Varian Utility Inova 600 NMR spectrometer. FAB mass spectra were recorded on a Zabspect high resolution magnetic mass spectrometer.

Preparation Example 1

2-(5-Methyl-2-phenyl-1,3-oxazol-4-yl)-ethanol (intermediate 1)

Methyl 4-bromo-3-pentanoate (23.2 g, 0.11 mol) and benzamide (20.1 g, 0.17 mol) were dissolved in 160 mL of toluene, and heated to reflux for 20 h. After concentration, the crude product obtained was purified with silica gel column chromatography (using n-hexane/EtOAc (6/1) as an eluent) to give 5.6 g of (5-methyl-2-phenyl-1,3-oxazol-4-yl)-acetic acid methyl ester as light brown oil with a yield of 22%.

(5-Methyl-2-phenyl-1,3-oxazol-4-yl)-acetic acid methyl ester (2.3 g, 10 mmol) was dissolved in 16 mL of Et$_2$O, and then added dropwise at 0° C. to a suspension of LiAlH$_4$ (0.38 g, 10 mmol) in Et$_2$O (4 mL). The solution was stirred at room temperature overnight, to which 0.4 mL H$_2$O, 0.4 mL of 15% NaOH solution, and 1.2 mL of H$_2$O, and a spoon of anhydrous MgSO$_4$ were carefully added in turn. The mixture was filtered, and the filtrate was concentrated to give 1.6 g of 2-(5-methyl-2-phenyl-1,3-oxazol-4-yl)-ethanol as a jasmine solid with a yield of 80%.

MS[M]+=231.2 m/e;
$^1$H-NMR (400 MHz, CDCl$_3$) δ 7.99~7.78 (m, 2H), 7.43~7.42 (m, 3H), 3.94 (t, 2H), 2.74 (t, 2H), 2.34 (s, 3H).

Preparation Example 2A (2S)-3-(4-hydroxy-phenyl)-2-tert-butoxycarbonylamino-propionic acid methyl ester (Intermediate 2A)

At 0° C., thionyl chloride (8 mL, 0.11 mmol) was added dropwise to a solution of methanol (100 mL) containing L-tyrosine (17.9 g, 0.1 mmol), before refluxing for 3 h. The resulting solution was concentrated, to which triethylamine (15 mL) and acetonitrile (150 mL) were added, followed by dropping of di-tert-butyl dicarbonate (BOC$_2$O) (23.3 mL, 0.11 mmol). Thereafter, the mixture was stirred for 1.5 h at room temperature. After concentration, the mixture was dissolved with dichloromethane (200 mL), and then washed with 1M NaHSO$_4$ aqueous solution (200 mL), a little of saturated sodium carbonate aqueous solution and water in turn. The organic layer was then dried over anhydrous MgSO$_4$, followed by concentration to give 26.0 g of (2S)-3-(4-hydroxy-phenyl)-2-tert-butoxycarbonylamino-propionic acid methyl ester as a white solid with a yield of 90%.

MS[M]+=295.4 m/e;
$^1$H-NMR (400 MHz, CDCl$_3$) δ 6.98~6.90 (m, 2H), 6.78~6.73 (m, 2H), 4.60~4.50 (m, 1H), 3.70 (s, 3H), 3.08~2.93 (m, 2H), 1.45 (s, 9H).

Preparation Example 2B (2S)-3-(3-Bromo-4-hydroxy-phenyl)-2-tert-butoxycarbonylamino-propionic acid methyl ester (Intermediate 2B)

At 0° C., a solution of bromine (0.9 g, 5.5 mmol) in glacial acetic acid (8 mL) was added dropwise to a suspension of L-tyrosine (1.0 g, 5.5 mmol) in glacial acetic acid (10 mL). The solution was stirred at room temperature overnight. The resulting mixture was filtered, and the filter cake was dried to obtain 1.7 g of a yellow solid, which was used directly in the next reaction.

The reaction was carried out by following the procedures described in Preparation Example 2A. The obtained crude product was further purified by silica gel column chromatography (using n-hexane/EtOAc (4/1) as an eluent) to give 0.8 g of Intermediate 2B as white solid with a yield of 38.6%.

MS[M]+=374.4 m/e;
$^1$H-NMR (400 MHz, DMSO-d$_6$) δ 7.37 (d, 1H), 7.10~7.05 (dd, 2H), 3.56 (s, 3H), 3.52~2.50 (m, 1H), 2.80~2.65 (m, 2H), 1.45 (s, 9H).

Preparation Example 3A (2S)-Amino-3-{4-[2-(5-methyl-2-phenyl-1,3-oxazol-4-yl)-ethoxy]-phenyl propionic acid methyl ester (Intermediate 3A)

Intermediate 1 (10.1 g, 0.05 mol), intermediate 2A (14.7 g, 0.05 mol) and triphenylphosphine (14.41 g, 0.055 mol) were dissolved with dried THF (180 mL), to which a solution of 40% diethyl azodicarboxylate (DIAD, 0.14 mmol) in toluene (74 mL) was dropped. The mixture was stirred at room temperature for 20 h before concentration. The residue was purified by silica gel column chromatography (using n-hexane/EtOAc (3/1) as an eluent) to give 16.8 g of (2S)-2-tert-butoxycarbonylamino-3-{4-[2-(5-methyl-2-phenyl-1,3-oxazol-4-yl)-ethoxy]-phenyl}-propionic acid methyl ester as light yellow oil with a yield of 67%.

(2S)-2-tert-Butoxycarbonylamino-3-{4-[2-(5-methyl-2-phenyl-1,3-oxazol-4-yl)-ethoxy]-phenyl}-propionic acid methyl ester (16.8 g, 0.035 mol), trifluoroacetic acid (34 mL) and dichloromethane (340 mL) were mixed with stirring at room temperature overnight. The mixture was neutralized with 0.5% NaOH aqueous solution. The organic layer was dried over anhydrous sodium sulfate, and then concentrated. The residue was purified by silica gel column chromatography (using CHCl$_3$/MeOH (80/1) as an eluent) to give 10.6 g of Intermediate 3A as light brown oil with a yield of 80%.

MS[M]+=380.4 m/e;
$^1$H-NMR (400 MHz, DMSO-d$_6$) δ 7.92~7.89 (m, 2H), 7.52~7.45 (m, 3H), 7.07 (d, 2H), 6.83 (d, 2H), 4.17 (t, 2H), 3.56 (s, 3H), 3.51~3.42 (m, 1H), 2.93 (t, 2H), 2.80~2.67 (m, 2H), 2.36 (s, 3H), 1.75 (s, 2H).

Preparation Example 3B (2S)-2-Amino-3-{3-bromo-4-[2-(5-methyl-2-phenyl-1,3-oxazol-4-yl)-ethoxy]-phenyl}-propionic acid methyl ester (Intermediate 3B)

Following the procedures described in the preparation of Intermediate 3A, intermediate 2B was used in place of intermediate 2A to give (2S)-2-Amino-3-{3-bromo-4-[2-(5-methyl-2-phenyl-1,3-oxazol-4-yl)-ethoxy]-phenyl}-propionic acid methyl ester.

MS[M]+=459.4 m/e;
$^1$H-NMR (400 MHz, DMSO-d$_6$) δ 7.92~7.89 (m, 2H), 7.52~7.48 (m, 3H), 7.37 (d, 1H), 7.10~7.05 (dd, 2H), 4.25 (t, 2H), 3.56 (s, 3H), 3.52~2.50 (m, 1H), 2.94 (t, 2H), 2.80~2.65 (m, 2H), 2.38 (s, 3H), 1.76 (s, 2H).

Example 1

(2S)-3-{4-[2-(5-methyl-2-phenyl-1,3-oxazol-4-yl)ethoxy]-phenyl}2-(3-phenyl-acryloylamino)-propionic acid Cinnamic acid (0.44 g, 3.0 mmol, purchased from Beijing Chemical Reagent Co.) and thionyl chloride (2 mL) was heated to reflux for 3 h, followed by evaporating thionyl chloride. The resulting residue was dissolved with 3 mL of anhydrous dichloromethane. In another reaction flask, Intermediate 3A (1.20 g, 3.1 mmol, self-made) and triethylamine (0.30 g, 3 mmol) were dissolved with dichloromethane (5 mL), to which the above solution was added dropwise at 0° C. The resulting solution was stirred at room temperature overnight, followed by concentration and purification with silica gel column chromatography (using n-hexane/EtOAc (3/1) as an eluent) to give 0.30 g (2S)-methyl 2-cinnamamido-3-(4-(2-(5-methyl-2-phenyl-1,3-oxazol-4-yl)ethoxy)phenyl)propanoate as a white solid with a yield of 20%.

The above-prepared white solid (0.30 g) was dissolved in THF (5 mL), to which 1N LiOH solution (2 mL) was added. The mixture was stirred at room temperature for 3 h, and then acidified with 2N HCl, followed by extracting with CHCl$_3$. The organic layer was dried, concentrated and recrystallized with acetone to give (2S)-3-{4-[2-(5-methyl-2-phenyl-1,3-oxazol-4-yl)-ethoxy]-phenyl}-2-(3-phenyl-acryloylamino)-propionic acid (0.27 g) as a white solid with the yield of 92% and mp of 207~209° C.

MS[M]+=496.4 m/e;
$^1$H-NMR (400 MHz, DMSO-d$_6$) δ 8.29 (d, 1H, J=8.3 Hz), 7.91~7.89 (m, 2H), 7.52~7.38 (m, 10H), 7.15~7.13 (m, 2H), 6.85~6.83 (m, 2H), 6.71 (d, 2H), 4.50 (m, 1H), 4.17 (t, 2H), 3.06~2.82 (m, 4H), 2.33 (s, 3H).

Example 2

(2S)-2-(2-fluoro-3-phenyl-acryloylamino)-3-{4-[2-(5-methyl-2-phenyl-1,3-oxazol-4-yl)-ethoxy]-phenyl}-propionic acid Following the procedures described in Example 1, 2-fluoro-3-phenyl acrylic acid was used in place of cinnamic acid to give (2S)-2-(2-fluoro-3-phenyl-acryloylamino)-3-{4-[2-(5-methyl-2-phenyl-1,3-oxazol-4-yl)-ethoxy]-phenyl}-propionic acid as a white solid with the yield of 21% and mp of 174~176° C.

MS[M]+=514.2 m/e;
$^1$H-NMR (400 MHz, DMSO-d$_6$) δ 12.87 (brs, 1H), 8.74 (d, 1H, J=8.1 Hz), 7.91~7.88 (m, 2H), 7.64~7.62 (m, 2H), 7.52~7.36 (m, 6H), 7.19~7.17 (d, 2H, J=8.1 Hz), 6.86~6.84 (m, 3H), 4.54~4.48 (m, 1H), 4.16 (t, 2H, J=6.6 Hz), 3.13~2.97 (m, 2H), 2.91~2.88 (t, 2H, J=6.6 Hz), 2.33 (s, 3H).

Example 3

(2S)-2-(3-(4-fluorophenyl)acryloylamino)-3-{4-[2-(5-methyl-2-phenyl-1,3-oxazol-4-yl)-ethoxy]-phenyl}-propanoic acid Following the procedures described in Example 1, 4-fluorocinnamic acid was used in place of cinnamic acid to give (2S)-2-(3-(4-fluorophenyl)acryloylamino)-3-{4-[2-(5-methyl-2-phenyl-1,3-oxazol-4-yl)-ethoxy]-phenyl}-propanoic acid as a white solid with the yield of 20% and mp of 188-190° C.

MS[M]+=514.4 m/e;
$^1$H-NMR (400 MHz, DMSO-d$_6$) δ 8.36 (1H, d), 7.90~7.88 (m, 2H), 7.75 (m, 4H), 7.49~7.42 (m, 4H), 7.15~7.13 (d, 2H), 6.85~6.82 (m, 3H), 4.52 (m, 1H), 4.15 (t, 2H, J=6.6 Hz), 3.08~2.84 (m, 4H), 2.33 (s, 3H).

Example 4

(2S)-3-{4-[2-(5-methyl-2-phenyl-1,3-oxazol-4-yl)-ethoxy]-phenyl}-2-(3-(2-(trifluoromethyl)-phenyl)-acryloylamino)propanoic acid Following the procedures described in Example 1, 2-(trifluoromethyl)cinnamic acid was used in place of cinnamic acid to give (2S)-3-{4-[2-(5-methyl-2-phenyl-1,3-oxazol-4-yl)-ethoxy]-phenyl}-2-(3-(2-(trifluoromethyl)-phenyl)-acryloylamino)propanoic acid as a white solid with the yield of 29% and mp of 170~172° C.

MS[M]+=564.4 m/e;

$^1$H-NMR (400 MHz, DMSO-$d_6$) δ 12.55 (brs, 1H), 8.42 (d, 1H, J=8.0), 7.89 (m, 2H), 7.81~7.44 (m, 8H), 7.13 (d, 2H, J=8.8 Hz), 6.86~6.75 (m, 3H), 4.54 (m, 1H), 4.18 (t, 2H, J=6.6 Hz), 3.08~2.82 (m, 4H), 2.33 (s, 3H).

Example 5

(2S)-2-[3-(3-chlorophenyl)acryloylamino]-3-{4-[2-(5-methyl-2-phenyl-1,3-oxazol-4-yl)-ethoxy]-phenyl}-propanoic acid Following the procedures described in Example 1, 3-chlorocinnamic acid was used in place of cinnamic acid to give (2S)-2-[3-(3-chlorophenyl)acryloylamino]-3-{4-[2-(5-methyl-2-phenyl-1,3-oxazol-4-yl)-ethoxy]-phenyl}-propanoic acid as a white solid with the yield of 30% and mp of 204~206° C.

MS[M]+=530.2 m/e;

$^1$H-NMR (400 MHz, DMSO-$d_6$) δ 8.28 (d, 1H, J=8.2 Hz), 7.89 (m, 2H), 7.60 (s, 1H), 7.49~7.40 (m, 7H), 7.13~6.78 (m, 2H), 6.86 (m, 3H), 4.50 (m, 1H), 4.17 (t, 2H, J=6.6 Hz), 3.28 (s, 1H), 3.05 (m, 1H), 2.90 (m, 3H), 2.34 (s, 3H)

Example 6

(2S)-3-{4-[2-(5-methyl-2-phenyl-1,3-oxazol-4-yl)-ethoxy]-phenyl}-2-[3-(3-(trifluoromethyl)phenyl)-acryloylamino]-propanoic acid Following the procedures described in Example 1, 3-(trifluoromethyl) cinnamic acid was used in place of cinnamic acid to give (2S)-3-{4-[2-(5-methyl-2-phenyl-1,3-oxazol-4-yl)-ethoxy]-phenyl}-2-[3-(3-(trifluoromethyl)phenyl)-acryloylamino]-propanoic acid as a white solid with the yield of 24% and mp of 214~216° C.

MS[M]+=564.2 m/e;

$^1$H-NMR (400 MHz, DMSO-$d_6$) δ 8.31~8.29 (d, 1H, J=8.2 Hz), 7.90~7.84 (m, 4H), 7.74~7.63 m, 4H), 7.54~7.42 (m, 4H), 7.20~7.10 (m, 2H), 6.90-6.80 (m, 3H), 4.50 (m, 1H), 4.17 (t, 2H, J=6.6 Hz), 3.10~2.82 (m, 4H), 2.35 (s, 3H).

Example 7

(2S)-2-[3-(3,4-difluorophenyl)acryloylamino]-3-{4-[2-(5-methyl-2-phenyl-1,3-oxazol-4-yl)-ethoxy]-phenyl}-propanoic acid Following the procedures described in Example 1, 3,4-difluorocinnamic acid was used in place of cinnamic acid to give (2S)-2-[3-(3,4-difluorophenyl)acryloylamino]-3-{4-[2-(5-methyl-2-phenyl-1,3-oxazol-4-yl)-ethoxy]-phenyl}-propanoic acid as a white solid with the yield of 34% and mp of 204~206° C.

MS[M]+−532.2 m/e;

$^1$H-NMR (400 MHz, DMSO-$d_6$) δ 12.68 (brs, 1H), 8.27 (d, 1H, J=8.1 Hz), 7.91~7.88 (m, 2Hl), 7.65~7.60 (m, 1H), 7.50~7.33 (m, 6H), 7.15~7.13 (d, 2H, J=8.6 Hz), 6.85~6.83 (d, 2H, J=8.6 Hz), 6.70~6.66 (d, 1H, J=15.6 Hz), 4.55~4.49 (m, 1H), 4.17 (t, 2H, J=6.6 Hz), 3.07~2.83 (m, 4H), 2.34 (s, 3H).

Example 8

(2S)-2-[3-(2,4-difluorophenyl)-acryloylamino]-3-{4-[2-(5-methyl-2-phenyl-1,3-oxazol-4-yl)-ethoxy]-phenyl}-propanoic acid Following the procedures described in Example 1, 2,4-difluorocinnamic acid was used in place of cinnamic acid to give (2S)-2-[3-(2,4-difluorophenyl)-acryloylamino]-3-{4-[2-(5-methyl-2-phenyl-1,3-oxazol-4-yl)-ethoxy]-phenyl}-propanoic acid as a white solid with the yield of 26% and mp of 199~201° C.

MS[M]+=532.2 m/e;

$^1$H-NMR (400 MHz, DMSO-$d_6$) δ 12.79 (brs, 1H), 8.47 (d, 1H, J=8.0 Hz), 7.92~7.89 (m, 2H), 7.74~7.66 (m, 1H), 7.55~7.30 (m, 5H), 7.20~7.10 (m, 3H), 6.88~6.70 (m, 3H), 4.50 (m 1H), 4.18 (t, 2H, J=6.6 Hz), 3.10~2.80 (m, 4H), 2.34 (s, 3H).

Example 9

(2S)-2-(3-(furan-2-yl)-acryloylamino)-3-{4-[2-(5-methyl-2-phenyl-1,3-oxazol-4-yl)-ethoxy]-phenyl}-propanoic acid Following the procedures described in Example 1, 3-furyl-2-yl-acrylic acid was used in place of cinnamic acid to give (2S)-2-(3-(furan-2-yl)-acryloylamino)-3-{4-[2-(5-methyl-2-phenyl-1,3-oxazol-4-yl)-ethoxy]-phenyl}-propanoic acid as a white solid with the yield of 28% and mp of 199-201° C.

MS[M]+=486.2 m/e;

$^1$H-NMR (400 MHz, DMSO-$d_6$) δ 12.66 (brs, 1H), 8.37~8.35 (d, 1H, J=8.1 Hz), 7.91~7.89 (m, 2H), 7.75 (d, 1H, J=1.7 Hz), 7.50~7.46 (m, 3H), 7.19~7.13 (m, 3H), 6.85~6.83 (d, 2H, J=8.7 Hz), 6.75~6.74 (m, 1H, J=3.3 Hz), 6.57~6.56 (m, 1H), 6.49~6.45 (d, 1H, J=14.7 Hz), 4.49~4.48 (m, 1H), 4.17 (t, 2H, J=6.4 Hz), 3.04~3.00 (m, 1H), 2.91~2.88 (t, 2H, J=6.4 Hz), 2.86~2.82 (q, 1H), 2.34 (s, 3H).

Example 10

(2S)-3-{3-bromo-4-[2-(5-methyl-2-phenyl-1,3-oxazol-4-yl)-ethoxy]-phenyl}-2-(3-p-tolylacryloylamino)-propanoic acid Following the procedures described in Example 1, Intermediate 3B was used in place of Intermediate 3A, and 4-methylcinnamic acid was used in place of cinnamic acid to give (2S)-3-{3-bromo-4-[2-(5-methyl-2-phenyl-1,3-oxazol-4-yl) ethoxy]-phenyl}-2-(3-p-tolylacryloylamino)-propanoic acid as a white solid with the yield of 24% and mp of 243~245° C.

MS (M)+=589.2 m/e;

$^1$H-NMR (400 MHz, DMSO-$d_6$) δ 12.77 (brs, 1H), 8.42 (d, 1H, J=8.1 Hz), 7.90~7.88 (m, 2H), 7.77~7.76 (m, 4H), 7.50~7.43 (m, 5H), 7.20~7.17 (m, 1H), 7.07~7.05 (d, 1H, J=16 Hz), 4.55 (m, 1H), 4.24 (t, 2H, J=6.6 Hz), 3.08~3.03 (m, 1H), 2.94~2.84 (m, 3H), 2.35 (s, 3H).

Example 11

(2S)-3-{3-bromo-4-[2-(5-methyl-2-phenyl-1,3-oxazol-4-yl)-ethoxy]-phenyl}-2-(2-fluoro-3-phenyl-acryloylamino)-propionic acid Following the procedures described in Example 1, Intermediate 3B was used in place of Intermediate 3A, and α-fluorocinnamic acid was used in place of cinnamic acid to give (2S)-3-{3-bromo-4-[2-(5-methyl-2-phenyl-1,3-oxazol-4-yl)-ethoxy]-phenyl}-2-(2-fluoro-3-phenyl-acryloylamino)-propionic acid as a white solid with the yield of 28% and mp: 243~245° C.

MS[M]+=593.4 m/e;

$^1$H-NMR (400 MHz, DMSO-$d_6$) δ 12.84 (brs, 1H), 8.66 (d, 1H, J=8.4 Hz), 7.89~7.87 (m, 2H), 7.62~7.60 (m, 2H), 7.49~7.35 (m, 7H), 7.21~7.19 (dd, 1H, J=2.2 Hz, J=2.0 Hz), 7.03 (d, 1H, J=8.6 Hz), 6.84~6.75 (d, 1H, J=38.7 Hz), 4.52~4.47 (m, 1H), 4.23 (t, 2H, J=6.4 Hz), 3.13~2.94 (m, 1H), 2.90 (t, 2H, J=6.4 Hz), 2.33 (s, 3H).

Example 12

(2S)-3-{3-bromo-4-[2-(5-methyl-2-phenyl-1,3-oxazol-4-yl)-ethoxy]-phenyl}-2-(3-(2,4-difluorophenyl)-acryloylamino)-propanoic acid Following the procedures described in Example 1, Intermediate 3B was used in place of Intermediate 3A, and 2,4-difluorocinnamic acid was used in place of cinnamic acid to give (2S)-3-{3-bromo-4-[2-(5-methyl-2-phenyl-1,3-oxazol-4-yl)ethoxy]-phenyl}-2-(3-(2,4-difluorophenyl)-acryloylamino)-propanoic acid as a white solid with the yield of 31% and mp of 221-223° C.

MS[M]+=611.4 m/e;

$^1$H-NMR (400 MHz, DMSO-$d_6$) δ 12.76 (brs, 1H), 8.43 (d, 1H, J=8.1 Hz), 7.91~7.88 (m, 2H), 7.72~7.70 (m, 1H), 7.51~7.28 (m, 6H), 7.06~7.04 (d, 1H. J=8.4 Hz), 6.76~6.72 (d, 1H, J=16 Hz), 4.55~4.49 (m, 1H), 4.24 (t, 2H, J=6.8 Hz), 3.07~3.02, 2.88~2.83 (m, 2H), 2.91 (t, 2H, J=6.8 Hz), 2.35 (s, 3H).

Example 13

(2S)-3-{3-bromo-4-[2-(5-methyl-2-phenyl-1,3-oxazol-4-yl)-ethoxy]-phenyl}-2-(2-fluoro-3-phenyl-acryloylamino)-propanoic acid Following the procedures described in Example 1, Intermediate 3B was used in place of Intermediate 3A, and 2-fluoro-3-phenyl-acrylic acid was used in place of cinnamic acid to give (2S)-3-{3-bromo-4-[2-(5-methyl-2-phenyl-1,3-oxazol-4-yl)-ethoxy]-phenyl}-2-(2-fluoro-3-phenyl-acryloylamino)-propanoic acid as a white solid with the yield of 25% and mp of 243~245° C.

MS[M]+=593.4 m/e;

$^1$H-NMR (400 MHz, DMSO-$d_6$) δ 12.84 (brs, 1H), 8.66 (d, 1H, J=8.4 Hz), 7.89~7.87 (m, 2H), 7.62~7.60 (m, 1H), 7.49~7.35 (m, 7H), 7.21~7.19 (d, 1H, J=2.2 Hz, J=2.0 Hz), 7.03 (d, 1H, J=8.6 Hz), 6.84~6.75 (d, 1H, J=38.7 Hz), 4.52~4.47 (m, 1H), 4.23 (t, 2H, J=6.4 Hz), 3.13~2.94 (m, 1H), 2.90 (t, 2H, J=6.4 Hz), 2.33 (s, 3H).

Example 14

Activity Assay of Compounds on Activating Human PPARα and PPARγ

The compounds were screened with respect to their functional effect of instantaneous transfection in 293-T cells, so that their capabilities of activating PPAR subtypes were determined. A chimeric receptor system as established in advance was used to compare the influence of receptor subtypes on the transcription activity of same target gene, with Rluc as an internal control to reduce the endogenous influence. Human PPARα and PPARγ ligand-binding domains were fused respectively with yeast transcription factor GAL4 DNA-binding domains, and then linked to expression vector pM of mammal, to thereby construct two plasmids pM-hPPARα/GAL4 and pM-PPARγ/GAL4. GAL4 DNA-binding area was linked to pB4-tk-luc, to thereby construct pB4-RES-tk-luc (a firefly luciferase reporter gene comprising GAL4 DNA-binding site). pRL-CMV-Rluc was used as an internal control to normalize transfection efficiency and endogenous influence.

293-T cells were incubated in a 48-well plate at a cell density of 2-4×10$^4$/well, using a phenol red-free and antibiotic-free 1640 medium containing 10% defatted fetal calf serum (FCS). After culturing for 48 h, the medium was replaced with a phenol red-free and antibiotic-free 1640 medium containing 5% defatted FCS, and then three plasmids pM-hPPAR/GAL4, pB4-RES-tk-luc and pRL-CMV-Rluc pertaining to two subtypes were respectively co-transfected into the 293-T cells. The strength of luciferase was measured at the time of 24 h after administration, with 0.2‰ DMSO as a blank control.

Features shown in broken lines show environmental structure and form no part of the claimed design.

| Compound | Effect of compounds (10 μM) on activation of PPARα and EC$_{50}$ Value | | |
|---|---|---|---|
| | Photon number (×10$^4$) | Increased multiple vs control | EC$_{50}$(μM) |
| Control | 2.1 | | |
| Example 7 | 8.6 | 4.1 | |
| Example 8 | 18.8 | 8.9 | 4.97 |
| Example 9 | 9.8 | 4.7 | 0.77 |
| Example 10 | — | — | |

| Compound | Effect of compounds (10 μM) on activation of PPARγ and EC$_{50}$ Value | | |
|---|---|---|---|
| | Photon number (×10$^4$) | Increased multiple vs control | EC$_{50}$(μM) |
| Control | 1.4 | | |
| Example 7 | 29.0 | 20.7 | |
| Example 8 | 27.6 | 19.7 | 1.16 |
| Example 9 | 23.7 | 16.9 | 0.074 |
| Example 10 | 24.1 | 17.2 | |

The invention claimed is:

1. A compound of formula I, racemate, optically active isomer, or pharmaceutically acceptable salt thereof,

I

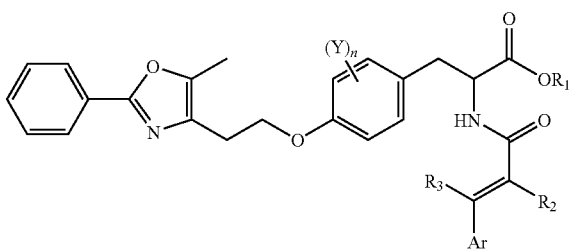

wherein
- $R_1$ is selected from hydrogen, $C_1$-$C_4$ straight or branched alkyl;
- $R_2$ and $R_3$ are independently selected from hydrogen, halogen, $C_1$-$C_4$ straight or branched alkyl;
- Ar is selected from mono-, di-, or tricyclic aromatic carbocyclic ring or heterocyclic ring containing 1 to 4 heteroatoms selected from a group consisting of O, S and N, wherein each single ring is 5- or 6-membered ring, and said ring may be unsubstituted or substituted with 1 to 5 of the following groups: halogen, nitro, hydroxy, hydroxymethyl, trifluoromethyl, trifluoromethoxy, $C_1$-$C_6$ straight or branched alkyl, $C_2$-$C_6$ straight or branched alkenyl, $C_1$-$C_4$ alkoxy, $C_2$-$C_4$ alkenoxy, phenoxy, benzyloxy, carboxyl or amino;
- Y is hydrogen or halogen; and
- n is an integer from 1 to 4.

2. A compound of claim 1, which is in S-configuration isomer of formula II,

II

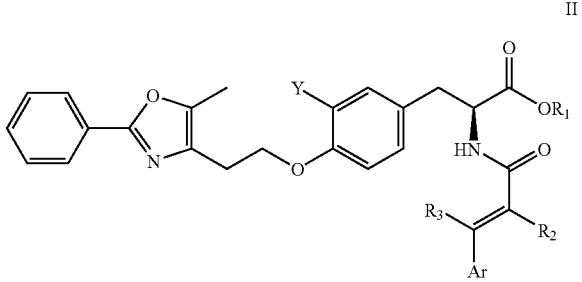

wherein:
- carbon atom bonded to $COOR_1$ is in the S configuration;
- $R_1$ is selected from hydrogen, $C_1$-$C_4$ straight or branched alkyl;
- $R_2$ and $R_3$ are independently selected from hydrogen, halogen, $C_1$-$C_4$ straight or branched alkyl;
- Ar is selected from mono-, di-, or tricyclic aromatic carbocyclic ring or heterocyclic ring containing 1 to 4 heteroatoms selected from a group consisting of O, S and N, wherein each single ring is 5- or 6-membered ring, and said ring may be unsubstituted or substituted with 1 to 5 of the following groups: halogen, nitro, hydroxy, hydroxymethyl, trifluoromethyl, trifluoromethoxy, $C_1$-$C_6$ straight or branched alkyl, $C_2$-$C_6$ straight or branched alkenyl, $C_1$-$C_4$ alkoxy, $C_2$-$C_4$ alkenoxy, phenoxy, benzyloxy, carboxyl or amino;
- Y is hydrogen or bromo;

or pharmaceutically acceptable salt thereof.

3. A compound of claim 1 selected from the group consisting of:
- (2S)-3-{-4-[2-(5-methyl-2-phenyl-1,3-oxazol-4-yl)-ethoxy]-phenyl}-2-(3-phenyl-acryloylamino)-propionic acid;
- (2S)-2-(2-fluoro-3-phenyl-acryloylamino)-3-{4-[2-(5-methyl-2-phenyl-1,3-oxazol-4-yl)-ethoxy]-phenyl}-propionic acid;
- (2S)-2-[3-(4-fluorophenyl)acryloylamino]-3-{4-(2-(5-methyl-2-phenyl-1,3-oxazol-4-yl)ethoxy)-phenyl}-propanoic acid;
- (2S)-3-{4-[2-(5-methyl-2-phenyl-1,3-oxazol-4-yl)-ethoxy]-phenyl)-2-(3-(2-(trifluoromethyl)phenyl)acryloylamino)-propanoic acid;
- (2S)-2-[3-(3-chlorophenyl)acryloylamino]-3-{4-[2-(5-methyl-2-phenyl-1,3-oxazol-4-yl)-ethoxy]-phenyl}-propanoic acid;
- (2S)-3-{4-[2-(5-methyl-2-phenyl-1,3-oxazol-4-yl)-ethoxy]-phenyl}-2-[3-(3-(trifluoromethyl)-phenyl)-acryloylamino]-propanoic acid;
- (2S)-2-[3-(3,4-difluorophenyl)-acryloylamino]-3-{4-[2-(5-methyl-2-phenyl-1,3-oxazol-4-yl)-ethoxy]-phenyl}-propanoic acid;
- (2S)-2-[3-(2,4-difluorophenyl)-acryloylamino]-3-{4-[2-(5-methyl-2-phenyl-1,3-oxazol-4-yl)-ethoxy]-phenyl}-propanoic acid;
- (2S)-2-(3-(furan-2-yl)acryloylamino)-3-{4-[2-(5-methyl-2-phenyl-1,3-oxazol-4-yl)-ethoxy]-phenyl}-propanoic acid;
- (2S)-3-{3-bromo-4-[2-(5-methyl-2-phenyl-1,3-oxazol-4-yl)-ethoxy]-phenyl}-2-(3-p-tolylacryloylamino)-propanoic acid;
- (2S)-3-{3-bromo-4-[2-(5-methyl-2-phenyl-1,3-oxazol-4-yl)-ethoxy]-phenyl}-2-(2-fluoro-3-phenyl-acryloylamino)-propionic acid;
- (2S)-3-{3-bromo-4-[2-(5-methyl-2-phenyl-1,3-oxazol-4-yl)-ethoxy]-phenyl}-2-[3-(2,4-difluorophenyl)acryloylamino]-propanoic acid; and
- (2S)-3-{3-bromo-4-[2-(5-methyl-2-phenyl-1,3-oxazol-4-yl)-ethoxy]-phenyl}-2-(2-fluoro-3-phenyl-acryloylamino)-propionic acid;

or pharmaceutically acceptable salts thereof.

4. A pharmaceutical composition comprising a compound of claim 1, a racemate, an optically active isomer, or a pharmaceutically acceptable salt thereof, and at least one pharmaceutically acceptable carrier.

5. A process for preparing a compound according to claim 1, comprising:
1) reacting a compound of formula III,

III

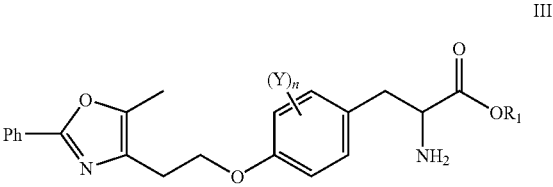

wherein Y, n and $R_1$ are the same as defined above in claim 1; with a compound of formula X,

X

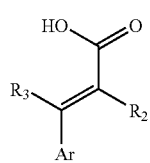

Ar, R$_2$ and R$_3$ are the same as defined above in claim 1, to obtain the compound of formula I,

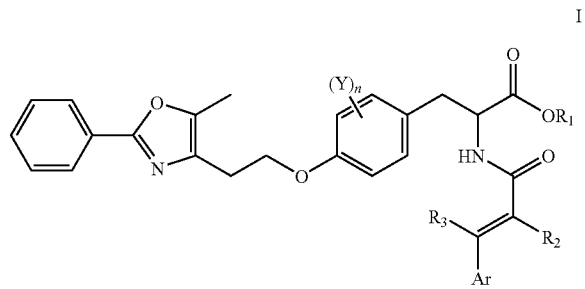

I wherein R$_1$, R$_2$, R$_3$, Ar, Y and n are the same as defined above in claim 1.

6. The process of claim 5, wherein the compound of formula III is prepared by the steps of:

1) subjecting a compound of formula IV and benzamide to a ring closure reaction to thereby obtain a compound of formula V; reducing the compound of formula V with lithium aluminum hydride (LiAlH$_4$) to obtain a compound of formula VI;

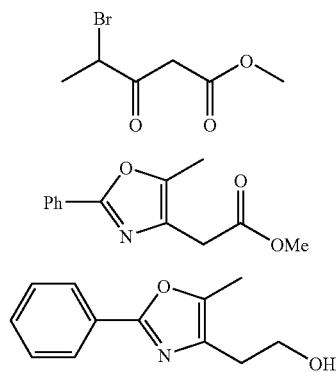

IV

V

VI 2) reacting the compound of formula VII wherein Y is hydrogen or halogen; n is an integer from 1 to 4 with R$_1$OH wherein R$_1$ is the same as defined above in claim 1 and SOCl$_2$, followed by reacting with BOC$_2$O, to obtain a compound of formula VIII wherein Y is hydrogen or halogen; n is an integer from 1 to 4 and R$_1$ is selected from hydrogen, C$_1$-C$_4$ straight or branched alkyl;

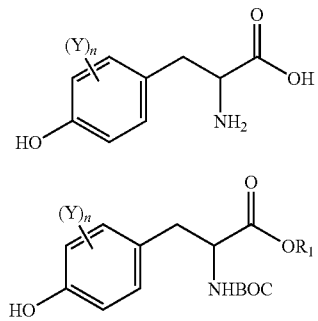

VII

VIII 3) reacting the compound of formula VI obtained in the step 1) with the compound of formula VIII obtained in the step 2) to obtain a compound of formula IX wherein Y, n and R$_1$ are as defined for formula VIII,

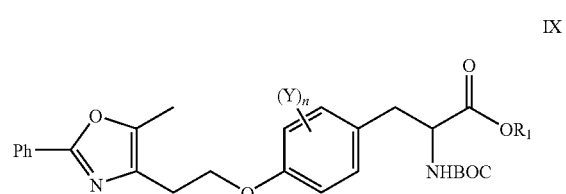

IX and then deprotecting the compound of formula IX with trifluoroacetic acid to give the compound of formula III,

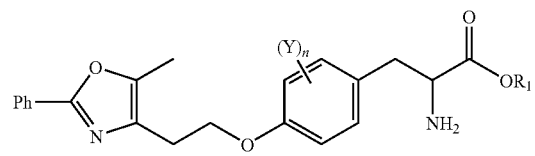

III wherein Y, n and R$_1$ are as defined for formula VIII.

7. The process of claim 5, further comprising:

reacting a compound of formula I

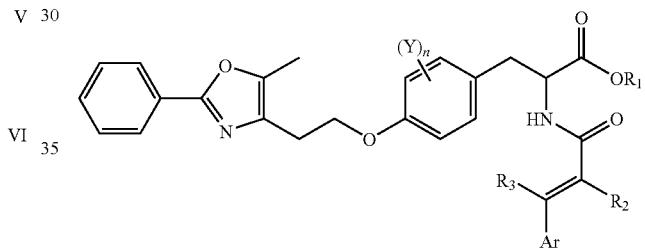

wherein R$_1$ represents C$_1$-C$_4$ straight or branched alkyl with an alkali metal hydroxide to give a compound of formula I wherein R$_1$ represents hydrogen.

8. A method for the treatment of hPPARγ and hPPARα mediated diseases, risk factors, or conditions which comprises administering to a subject in need thereof a therapeutically effective amount of a compound as claimed in claim 1.

9. The method according to claim 8, wherein the diseases, risk factors, or conditions are selected from hyperglycemia, dyslipidemia, type II diabetes mellitus including associated diabetic dyslipidemia.

10. A compound of claim 3, wherein the carbon atom bounded to the carboxy group ROOR$^1$ is in the S configuration.

* * * * *